United States Patent [19]

Becht

[11] 4,196,836

[45] Apr. 8, 1980

[54] SURGICAL STAPLING INSTRUMENT

[75] Inventor: Carl T. Becht, Cincinnati, Ohio

[73] Assignee: Senco Products Inc., Cincinnati, Ohio

[21] Appl. No.: 877,791

[22] Filed: Feb. 14, 1978

[51] Int. Cl.² .................... B25C 5/02; B31B 1/00; F24C 15/16

[52] U.S. Cl. .................... 227/110; 128/334 R; 227/19

[58] Field of Search .................... 128/305, 337, 334 R; 227/19, 119, 110, 148

[56] References Cited

U.S. PATENT DOCUMENTS

| Re. 28,932 | 8/1976 | Noiles et al. | 227/19 |
|---|---|---|---|
| 3,618,842 | 11/1971 | Bryan | 227/19 |
| 3,638,847 | 2/1972 | Noiles et al. | 227/19 |
| 3,643,851 | 2/1972 | Green et al. | 227/19 |
| 3,650,453 | 3/1972 | Smith, Jr. | 227/19 |
| 3,662,939 | 5/1972 | Bryan | 227/19 |
| 3,717,294 | 2/1973 | Green | 227/19 |
| 3,837,555 | 9/1974 | Green | 227/19 |
| 4,043,504 | 8/1977 | Hueil et al. | 227/19 |

Primary Examiner—Robert W. Michell
Assistant Examiner—C. W. Shedd
Attorney, Agent, or Firm—Frost & Jacobs

[57] ABSTRACT

A surgical stapling instrument for forming and implanting a staple in the skin or fascia of a patient to close a wound or incision therein. The surgical stapling instrument is intended to be used with a staple carrying cartridge of the type taught in U.S. Pat. No. 4,043,504 and characterized by a staple feeding track containing a stack of staples, a parallel staple forming tack, a longitudinally shiftable feeder actuator operative to cause the bottommost staple of the stack to be shifted from the staple feeding track to the staple forming track and a longitudinally shiftable staple former to implant the staple and form it about an anvil mounted on the instrument. The surgical stapling instrument has a handle portion and a nose portion rotatively mounted in the handle portion and capable of being set and remaining in any rotative position with respect to the handle portion. The nose portion carries the instrument anvil and releasably supports the surgical staple carrying cartridge. The nose portion also mounts a longitudinally shiftable feeder block operatively connected to the cartridge feeder actuator and a longitudinally shiftable driver operatively connected to the cartridge staple former. A trigger is mounted in the handle portion and is operatively connected to the driver to shift the driver to cause the cartridge staple former to form and implant a staple. A feeder pawl causes the feeder block to travel with the driver during the driver's initial travel to operate the cartridge feeder actuator to provide a staple for the cartridge staple former to implant and form.

13 Claims, 22 Drawing Figures

_FIG 17_

SURGICAL STAPLING INSTRUMENT

BACKGROUND OF THE INVENTION

1. Field of the Invention

The invention relates to a surgical stapling instrument and more particularly to a surgical stapling instrument for use with a staple carrying cartridge of the type taught in U.S. Pat. No. 4,043,504.

2. Description of the Prior Art

Recently, surgeons have come more and more to the use of staples, rather than conventional thread sutures, for closing wounds or incisions in the skin or fascia of a patient. This trend is due largely to the fact that the use of staples is a far easier procedure and, of even greater importance, is very much faster. This substantially reduces the time required for suturing and the length of time the patient must be maintained under anaesthesia.

Prior art workers have developed various types of surgical stapling instruments and staple cartridges for use therewith, as are exemplified by U.S. Pat. No. RE 28,932; 3,618,842; 3,638,847; 3,643,851; 3,650,453; 3,662,939; 3,717,294 and 3,837,555. The complexity of prior art staple cartridges has been reflected in the complexity and expense of the surgical stapling instruments with which the cartridges are used. The use of complicated gear means or the staple former itself to advance the staples within the cartridge has hitherto required considerable power from the surgical stapling instrument.

The staple carrying cartridge taught in U.S. Pat. No. 4,043,504 constitutes a very much simpler, less expensive and more reliable staple carrying cartridge in which the staples are far less likely to become jammed. The staple carrying cartridge is so arranged that the staple feeding portion of its cycle is completed before the start of the staple forming portion of its cycle.

The surgical stapling instrument of the present invention has been developed specifically for use with the staple carrying cartridge of the above mentioned U.S. Pat. No. 4,043,504. The surgical stapling instrument is provided with a staple forming anvil separate from the staple carrying cartridge. The staple carrying cartridge is mounted on a nose portion of the surgical stapling instrument and means are provided to prevent actuation of the surgical stapling instrument unless and until the staple carrying cartridge is properly mounted on its nose portion. The surgical stapling instrument is provided with a driver and is so constructed as to transmit a manually applied force to the driver so that initial movement of the driver completes the feed cycle of the staple carrying cartridge, further movement of the driver initiating and completing the staple forming portion of the cartridge cycle. A ratchet mechanism is provided in the surgical stapling instrument to prevent reactivation of the staple feed portion of the staple carrying cartridge cycle until the staple forming portion of the staple carrying cartridge cycle has been completed.

The surgical stapling instrument is provided with a latch to maintain the staple carrying cartridge in place on its nose portion. Attachment of the staple carrying cartridge to the instrument nose portion is rendered particularly secure by virtue of the fact that the latch means provides two thrust points, one securely positioning the cartridge with respect to the instrument anvil and the other securely positioning the cartridge against the instrument nose.

The nose portion of the instrument is mounted to the handle portion on resilient bushings so as to be rotatable with respect to the handle portion throughout 360°, while maintaining any rotative position with respect to the handle portion to which the nose portion has been set by the surgeon.

SUMMARY OF THE INVENTION

The surgical stapling instrument of the present invention is particularly adapted for use with a staple carrying cartridge of the type taught in U.S. Pat. No. 4,043,504 and comprises a handle portion and a nose portion. The nose portion of the instrument carries at its free end the instrument anvil about which the surgical staples are formed. The nose portion also releasably supports the surgical staple carrying cartridge. Latch means on the instrument urge the staple carrying cartridge both against the anvil and the instrument nose portion. The surgical stapling instrument is provided with a lock-out pawl which prevents actuation of the instrument unless a staple carrying cartridge is properly and securely mounted to its nose portion.

A feeder block is so mounted in the nose portion of the instrument as to be longitudinally shiftable. The feeder block is provided with a feeder pin adapted to engage and actuate the staple feeding mechanism of the staple carrying cartridge. A driver is also mounted in the instrument nose portion so as to be longitudinally shiftable. The driver is provided with a lug adapted to engage and actuate the staple former of the staple carrying cartridge.

The surgical stapling instrument has a trigger mounted in its handle portion and operatively connected to the driver. Actuation of the trigger will cause a longitudinal shifting of the driver. A feeder pawl is pivotally mounted on the feeder block and acts to cause the feeder block to shift with the driver during the initial portion of the longitudinal movement of the driver so as to activate the staple feeding mechanism of the staple carrying cartridge. During further longitudinal movement of the driver, the feeder pawl disengages the feeder block from the driver and the driver thereafter activates the staple former of the cartridge.

A ratchet mechanism within the handle portion of the instrument prevents reactivation of the feeder block and thus the staple feeding mechanism of the cartridge until the instrument driver has completed its travel to cause the cartridge former to form and implant the already fed surgical staple.

Finally, the nose portion of the instrument is rotatively mounted in the handle portion in such as way that it may be set at, and will remain at, any rotative position with respect to the handle portion, depending upon the preference of the surgeon and the nature of the wound or incision to be closed.

BRIEF DESCRIPTION OF THE DRAWINGS

FIG. 4 is a front elevational view of an exemplary surgical staple to be used with the instrument of the present invention.

FIG. 5 illustrates the surgical staple of FIG. 4 in its fully formed condition.

FIG. 6 is a cross sectional view of the surgical instrument taken along section line 6—6 of FIG. 2.

FIG. 7 is a fragmentary rear elevational view of the surgical stapling instrument nose.

FIG. 15 is an end elevational view of the latch of FIG. 14.

FIG. 16 is an enlarged, fragmentary, cross sectional view illustrating the staple cartridge latch and the lockout pawl in their respective positions prior to the mounting of a staple cartridge on the instrument nose portion.

FIG. 18 is an enlarged fragmentary, cross sectional view showing the components of the drive mechanism in their respective positions just prior to completion of the staple feed portion of the staple carrying cartridge cycle.

FIG. 19 is an enlarged, fragmentary, cross sectional view showing the components of the drive mechanism in their respective positions just after completion of the staple feed portion of the staple carrying cartridge cycle.

DESCRIPTION OF THE PREFERRED EMBODIMENTS

Figures 1, 4A, 4B:
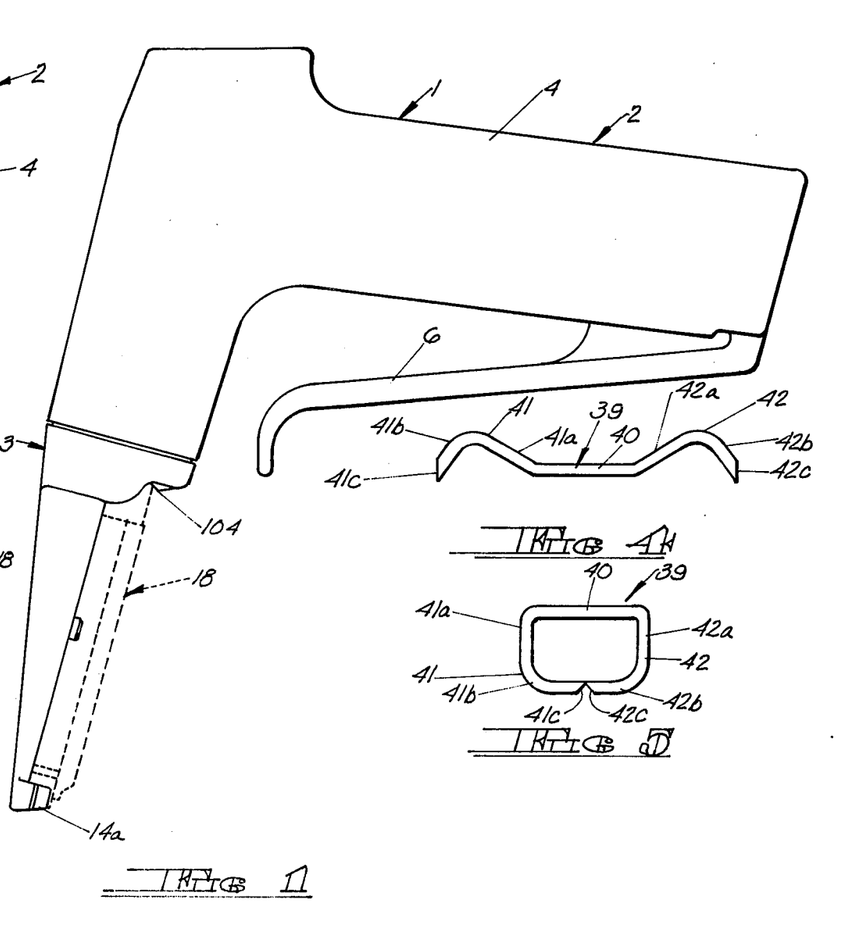
FIG. 1 is a side elevational view of the surgical stapling instrument of the present invention with a staple carrying cartridge illustrated in broken lines.
Figures 2, 3:
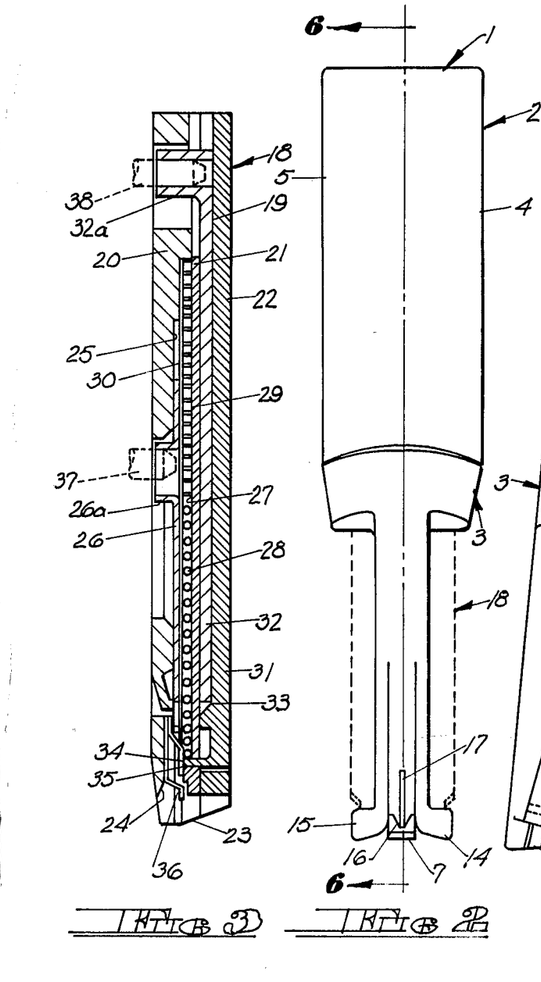
FIG. 2 is a front elevational view of the surgical stapling instrument of FIG. 1 with a staple cartridge shown in broken lines.
FIG. 3 is a cross sectional view of a staple cartridge of the type to be used with the surgical stapling instrument of the present invention.
Figure 2:
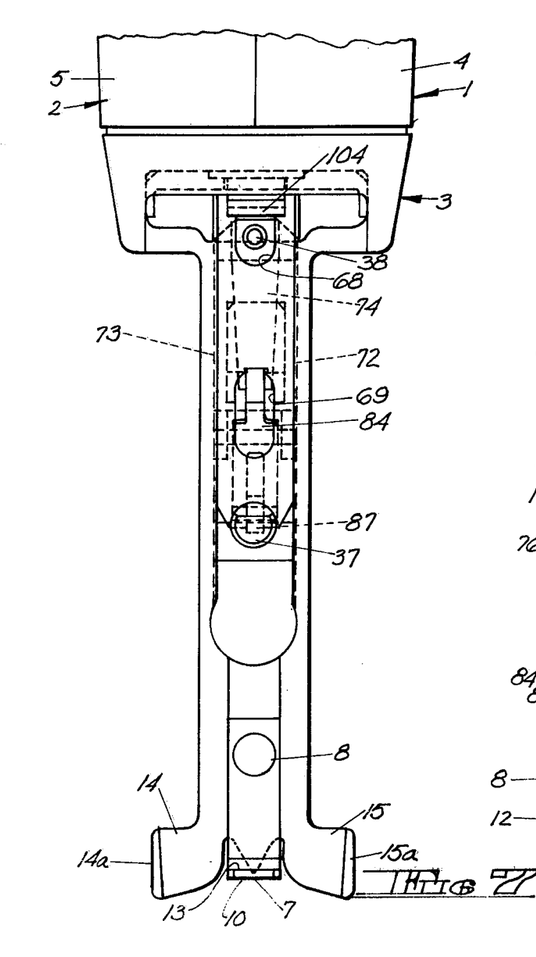
Figure 3:
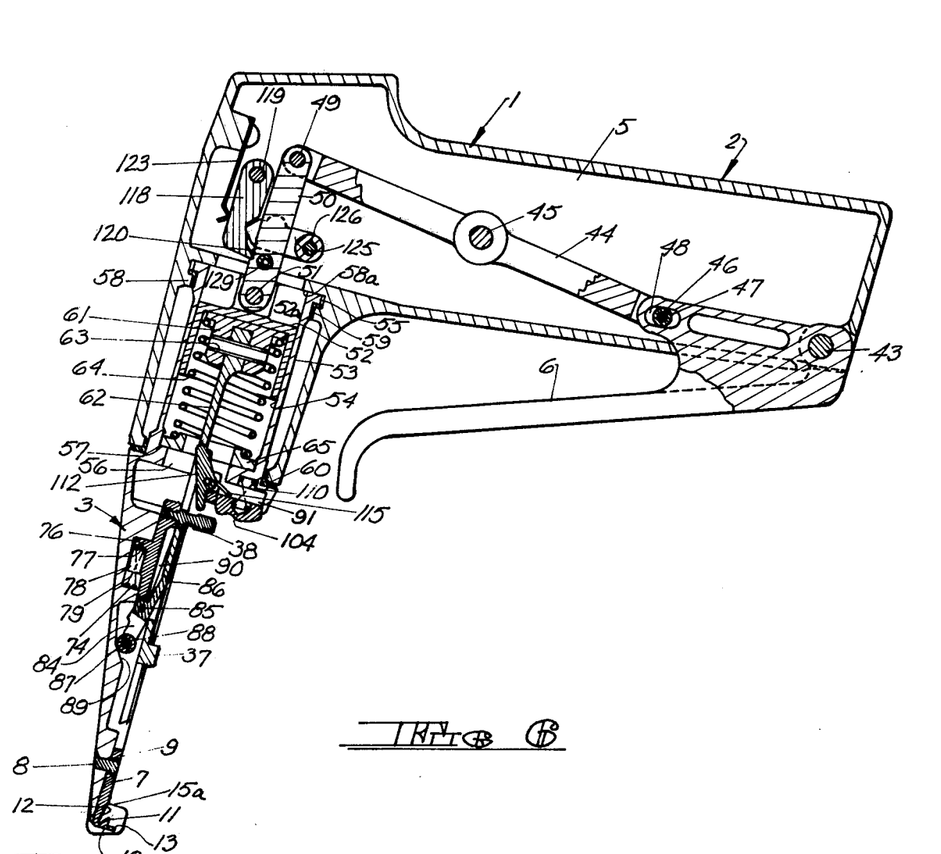

In all of the Figures, like parts have been given like index numerals. Reference is first made to FIGS. 1 and 2 wherein the surgical stapling instrument of the present invention is generally indicated at 1. The surgical stapling instrument 1 is composed of a handle portion generally indicated at 2 and a nose portion generally indicated at 3. The handle portion may be made of two halves 4 and 5 (see FIG. 2) suitably fastened together by any appropriate means such as one or more machine screws (not shown), or the like. An actuator or trigger 6 is mounted within the handle portion 2.

Referring now to FIGS. 1, 2, 6 and 7, the free end of nose portion 3 carries an anvil 7. The anvil 7 may constitute an integral part of the instrument nose portion 3, or it may be a separate element, as illustrated, affixed to the nose portion 3 by any appropriate means such as rivet 8.

Figure 20:
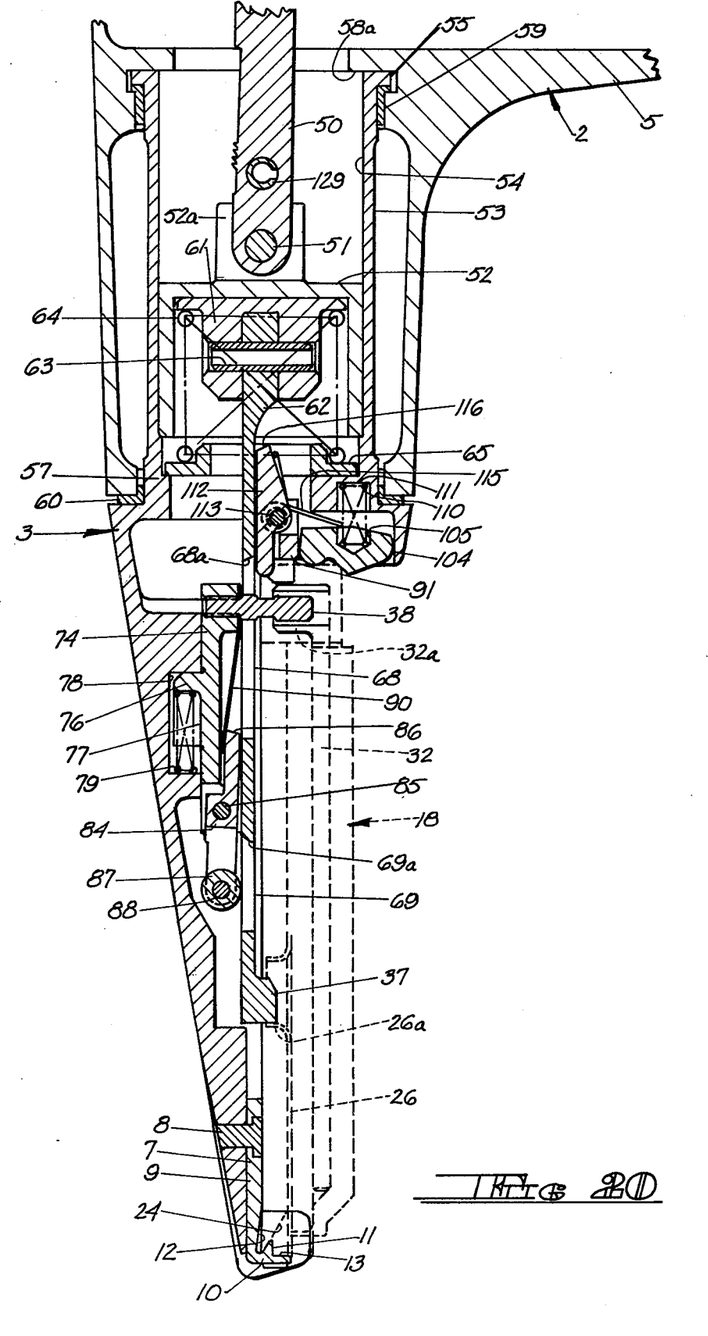
FIG. 20 is an enlarged, fragmentary, cross sectional view showing the components of the drive mechanism of the surgical stapling instrument in their respective positions at completion of the staple forming portion of the staple carrying cartridge cycle and prior to their return to their normal, at-rest positions.

For purposes of an exemplary showing, the anvil 7 is illustrated as being of the type taught in copending application Ser. No. 822,049, filed Aug. 5, 1977, in the names of J. Charles Hueil, Robert G. Rothfuss and Terry A. Boothby and entitled ANVIL ATTACHMENT FOR A SURGICAL STAPLING INSTRUMENT. Briefly, the anvil 7 is generally "L-shaped" (see FIG. 6). A first leg 9 of the anvil 7 is adapted to lie along and to be affixed to the nose portion 3 of the surgical stapling instrument 1 as described. The second leg 10 of the anvil 7 extends laterally of nose portion 3. Near the juncture of legs 9 and 10, the leg 10 is provided on its upper surface with an upstanding wedge-shaped lug 11 which, in cooperation with an adjacent relief 12 on leg 9, engages and maintains the lower end of the staple carrying cartridge (see FIG. 20). The upper surface of leg 10, adjacent lug 11, is provided with at least one anvil surface 13 adapted to abut and support the crown of a surgical staple during a staple forming operation. The anvil 7 may be provided with more than one anvil surface, to accommodate staples of different sizes, as is taught in the above noted copending application.

The lowermost portion of the instrument nose 3 may be provided with lateral extensions or wings 14 and 15 having rearwardly extending flanges 14a and 15a. The wings 14 and 15 and flanges 14a and 15a serve to protect the anvil 7 and to permit the surgical stapling instrument 1 to be set down upon its side or set down upon flanges 14a and 15a and the base of trigger 6 without contact between the anvil 7 and the surface upon which the surgical stapling instrument 1 is rested. That portion of the instrument nose 3 located between wings 14 and 15 may have a pointed configuration as at 16 (see FIGS. 2 and 7) and an indicia center line 17 to assist the surgeon in properly aligning the nose portion 3 and the anvil 7 with the wound or incision to be closed.

Reference is again made to FIGS. 1 and 2. The nose portion 3 of the surgical stapling instrument 1 is adapted to support a staple carrying cartridge of the type taught in U.S. Pat. No. 4,043,504. Such a cartridge is generally indicated at 18 (in broken lines) in its mounted position on nose portion 3, in FIGS. 1 and 2. In order to fully appreciate the nature and workings of the surgical stapling instrument of the present invention, it is believed that an understanding of the staple carrying cartridge of U.S. Pat. No. 4,043,504 is required. To this end, such a cartridge (again generally indicated at 18) is shown in cross section in FIG. 3.

Briefly, the staple carrying cartridge 18 has a body 19 made up of three basic parts between which all of the remaining parts are located. These basic parts comprise a staple former housing 20, a staple housing 21 and a horizontal feeder housing 22. All three of these parts are configured at their bottom end to provide a tapered notch 23 to just nicely receive the leg 10 of anvil 7. The staple former housing 20 has, at its lower end, a downwardly and rearwardly sloping surface 24 adapted to cooperate with the sloping surface of anvil lug 11.

The staple former housing 20 provides a staple forming track 25. A staple former 26 is slidably mounted in the staple former track 25. The staple housing has a staple feeding track 27 formed therein adapted to receive a stack of staples 28 and accommodating a sinuous staple advancing spring 29. The staple forming track 25 and the staple feeding track 27 are separated from each other by a thin divider wall 30.

The horizontal feeder housing 22 has an integral resilient tine portion 31 constituting a horizontal feeder. The horizontal feeder housing 22 also slidably mounts a feeder actuator 32 which cooperates with a cam surface 33 on the horizontal feeder 31 to shift the horizontal feeder 31 from its normal position as shown in FIG. 3 toward the right as viewed in that Figure.

The bottom edge of the divider wall 30 and the adjacent portions of the staple housing 21 are configured so as to provide a horizontal passage or "window" 34 through which the bottommost staple of the stack 28 may pass from the staple feeding track 27 to the staple forming track 25. It will be noted that when the horizontal feeder 31 is in its normal position as shown in FIG. 3, it extends into the staple feeding track 27 and underlies the bottommost staple of the stack 28. Spring means 35 serves to normally close the window 34 and, in addition, cooperate with the horizontal feeder 31 to hold a staple in the staple former track 25 in proper position to be engaged by staple former 26. A second spring means 36 is mounted in the staple former housing 20 and assists in disengaging a formed staple from the anvil 7. It will be noted that the staple former 26 has a driving eyelet 26a extending through an appropriately configured opening in the staple former housing 20 and adapted to be engaged by a lug on the driver of the surgical stapling instrument 1, as will be described hereinafter. Such a driver lug is illustrated in broken lines at 37 in FIG. 3. In similar fashion, the feeder actuator 32 is provided with a driving eyelet 32a extending through appropriate openings in the staple housing 21 and the staple former housing 20 and adapted to be engaged by a feeder pin of the surgical stapling instrument 1, as will be described hereinafter. Such a feeder pin is shown in broken lines at 38.

In operation, the surgical stapling instrument feeder pin 38 first shifts the feeder actuator 32 downwardly to cause the horizontal feeder 31 to shift out of staple feeding track 27. This permits the lowermost staple of stack 28 to drop under the influence of sinuous spring 29 to a position adjacent window 34. Thereafter, the horizontal feeder actuator 32 is returned by the surgical stapling instrument feeder pin 38 to the position shown in FIG. 3. This permits the horizontal feeder 31 to return to its normal position as shown in FIG. 3, resulting in the fact that the lowermost staple of stack 28 is shoved through window 34 and is held in the staple forming track 25 between the end of the horizontal feeder 31 and the spring means 35. In the meantime, driver lug 37 has caused the staple former 26 to begin a downward movement. Even though the instrument driver lug 37 and feeder pin 38 initially move downward simultaneously, the driving eyelet 26a of the staple cartridge former 26 is elongated and it is not until feeder actuator 32 has returned to the position shown in FIG. 3 that the driving eyelet 26a of staple former 26 is contacted by the instrument driver lug 37. Continued downward movement of lug 37 results in the staple former 26 causing the staple to be formed about anvil surface 13 (see FIG. 6 and 7) of anvil 7. The surgical stapling instrument driver lug 37 at this point causes the staple former 26 to return to its normal position as illustrated in FIG. 3, thereby ending the cycle of the staple carrying cartridge 18. Spring means 36 assists in disengaging the formed staple from the anvil 7.

The surgical stapling instrument may be used to form and implant any surgical staple appropriate for use with the cartridge 18. While not intended to constitute a limitation on the present invention, for purposes of an exemplary showing a surgical staple of the type taught in U.S. Pat. No. 4,014,492 is illustrated in FIG. 4 and is generally designated by index numeral 39. The staple 39 of FIG. 4 comprises a crown portion 40 terminating in legs 41 and 42. Legs 41 and 42 have first upwardly and outwardly sloping portions 41a and 42a, terminating in second downwardly and outwardly sloping portions 41b and 42b. The staple points 41c and 42c are formed by diagonal cuts across the leg ends. As explained in the above identified U.S. Pat. No. 4,014,492, the cuts forming points 41c and 42c are so arranged as to be substantially perpendicular to the anvil surface 13 of anvil 7 (see FIGS. 6 and 7) about which the staple is to be formed and substantially perpendicular to the skin or fascia of the patient. FIG. 5 illustrates the staple 39 of FIG. 4 in its fully formed condition.

Turning now to FIG. 6, the surgical stapling instrument trigger 6 is pivotally mounted at its base within the instrument handle portion 2 by pivot pin 43. An elongated main lever 44 is pivotally mounted within handle portion 2 by pivot pin 45. One end of main lever 44 is connected to trigger 6 by means of pin 46 and bushing 47 located in elongated slot 48 in trigger 6. The other end of main lever 44 is pivotally connected by pin 49 to one end of a connecting rod 50. The other end of connecting rod 50, in turn, is pivotally attached by pin 51 to an extension 52a on a guide piston 52.

The upper end of nose portion 3 is cylindrical as at 53, providing a cylindrical bore 54 within which guide piston 52 is slidably mounted. The upper cylindrical part of nose portion 3 is open at its upper end and is provided at its upper end with an annular flange 55. The cylindrical upper part 53 of nose portion 3 is also open at its lower end as at 56 providing an annular shoulder 57.

Adjacent the upper annular flange 55 on nose portion, the handle portion 2 has two interior annular flanges 58 and 58a. Cooperation of flanges 55 and 58 render nose portion 3 rotatively captive within handle portion 2. Resilient bushings are provided as at 59 and 60. Resilient bushings 59 and 60 are made of material such as nylon or the like and are sufficiently resilient to allow smooth rotation of nose portion 3 with respect to handle portion 2, and are at the same time tight enough to hold the nose portion 3 in any desired rotative position with respect to handle portion 2 set by the surgeon on the basis of the nature and location of the would or incision to be closed and the surgeon's own personal preference.

Housed inside the guide piston 52 and in abutting relationship therewith, there is a driver coupling 61. The uppermost end of the surgical stapling instrument driver 62 is attached to driver coupling 61 by pin 63. The driver coupling 61 is maintained in abutting relationship with guide piston 52 by means of compression spring 64. As can be seen from FIG. 6, the upper end of compression spring 64 abuts driver coupling 61, while the lower end of compression spring 64 rests on a spring plate 65 which, in turn, is mounted on the annular shoulder 57 of nose portion 3.

It will be understood by one skilled in the art that the guide piston 52 and driver coupling 61 cooperate to permit the above mentioned rotation of the nose portion 3 with respect to the handle portion 2 since the driver coupling 61 and the driver 62 are rotatable with the nose portion 3, while the guide piston 52 is not.

Figures 8, 10, 11:
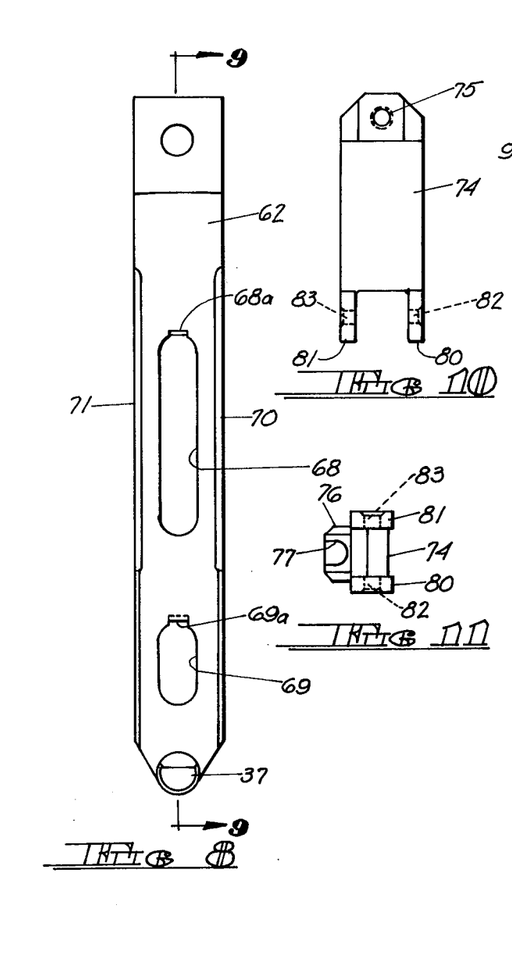
FIG. 8 is an elevational view of the surgical stapling instrument driver.
FIG. 10 is an elevational view, of the feeder block of the surgical stapling instrument.
FIG. 11 is an end view of the feeder block of FIG. 10.
Figure 9:
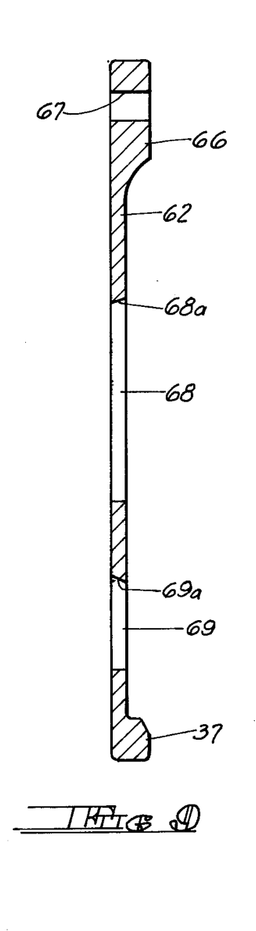
FIG. 9 is a cross sectional view taken along section line 9—9 of FIG. 8.
Figure 10:
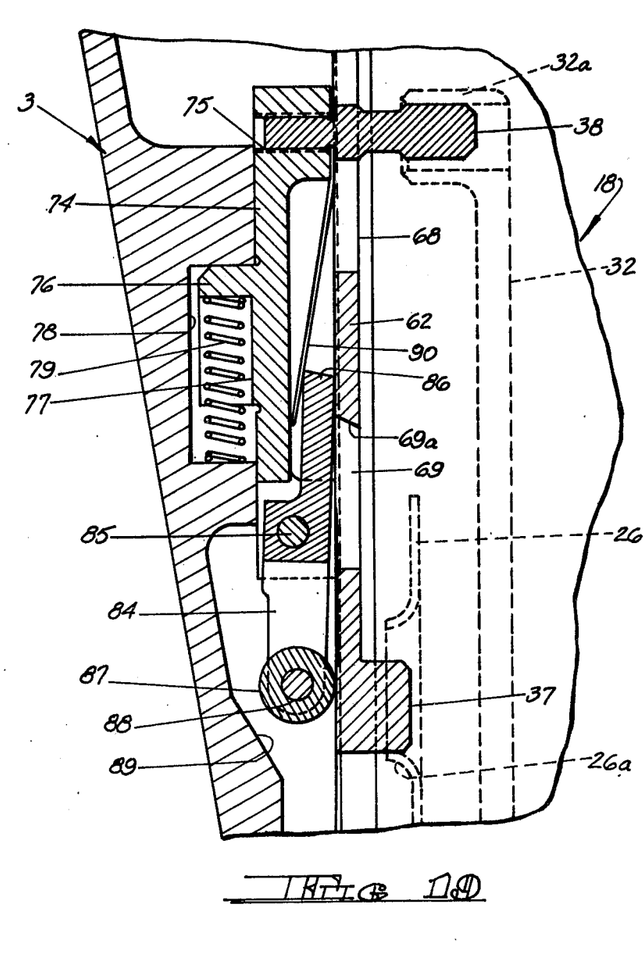
Figure 11:
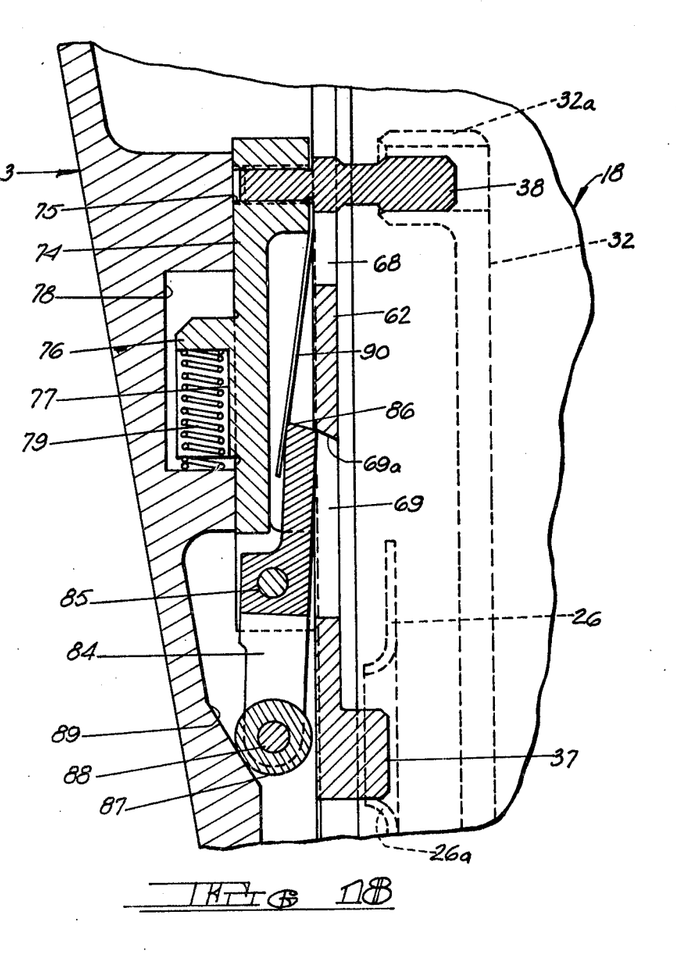

The surgical stapling instrument driver 62 is most clearly shown in FIGS. 8 and 9. The driver 62 comprises an elongated, narrow plate-like element. At its upper end, it is of enlarged thickness as at 66 and is provided with a transverse bore 67 to receive the pin 63 by which it is attached to the driver coupling 61. At its lowermost end, the driver 62 is provided with the driver lug 37 adapted to be received within the elongated driving eyelet 26a of the cartridge staple former 26 (see FIG. 3).

The driver 62 has a first elongated slot 68 which accommodates the feeder pin 38 (which will be described hereinafter) and the lock-out pawl of the surgical stapling instrument to be described hereinafter. The uppermost end 68a of slot 68 is sloped upwardly and rearwardly to provide an abutment surface for the instrument lock-out pawl as will be evident hereinafter.

A second elongated slot 69 is provided in the driver 66 which is intended to accommodate the feeder pawl to be described hereinafter. The uppermost end of slot 69 slopes upwardly and forwardly to provide an abutment surface 69a, the purpose of which is to be described.

The longitudinal edges of driver 62 are chamfered or beveled as at 70 and 71. Since the driver 62 is adapted to be longitudinally shiftable within nose portion 3 by guide piston 52, The edge portions 70 and 71 of the driver are intended to cooperate with the guiding undercut edges 72 and 73 (FIG. 7) of nose portion 3.

A feeder block 74 is slidably mounted in nose portion 3. The feeder block can best be seen in FIGS. 10 and 11. The uppermost end of the feeder block is provided with a threaded bore 75 adapted to receive the threaded end of feeder pin 38 (see FIG. 6). The front surface of feeder block 74 slidably engages the inside surface of nose portion 3. The feeder block 74 is retained within the nose portion 3 by driver 62. The front surface of feeder block 74 is provided with an extension 76 having a socket 77 formed therein. The socket is received in a notch 79 (see FIG. 6) in nose portion 3. A compression spring 79 is mounted in notch 78 with its upper end abutting the upper end of socket 77 and its lower end abutting the lower end of notch 78. Compression spring 79 biases feeder block 74 to its uppermost position as illustrated in FIG. 6.

The lowermost end of feeder block 74 has downwardly extending bifurcations 80 and 81, provided with coaxial perforations 82 and 83, respectively. A feeder pawl 84 (FIG. 6) is pivotally mounted between bifurcations 80 and 81 of feeder block 74 by means of pivot pin 85 (FIG. 6) passing through the coaxial perforations 82 and 83 of feeder block 74. The uppermost end of feeder pawl 85 is provided with a nose 86 adapted to cooperate with the uppermost surface 69a of slot 69 in driver 62, as will be described hereinafter. The lowermost end of feeder pawl 84 is provided with a bushing 87 rotatively affixed thereto by pivot pin 88. The bushing 87 is adapted to cooperate with the downwardly and rearwardly sloping inner surface 89 of instrument nose portion 3, as will be described hereinafter. The feeder pawl 84 is biased toward driver 62 and its normal position illustrated in FIG. 6 by leaf spring 90. The uppermost end of leaf spring 90 is attached to feeder block 74 by virtue of the fact that feeder pin 38 passes through a perforation in the uppermost end of leaf spring 90. The lowermost free end of the leaf spring 90 bears against the upper portion of the feeder pawl 84.

Figure 12:
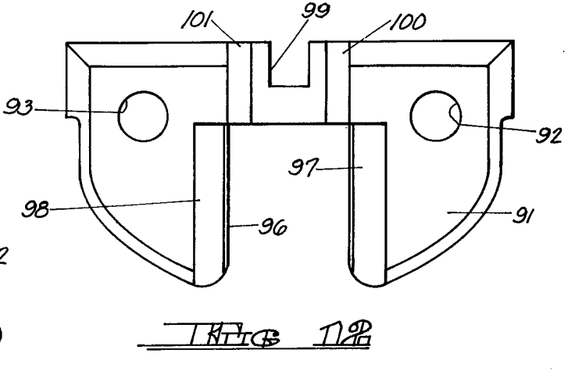
FIG. 12 is a plan view of the staple cartridge latch retainer plate of the surgical stapling instrument.
Figure 13:
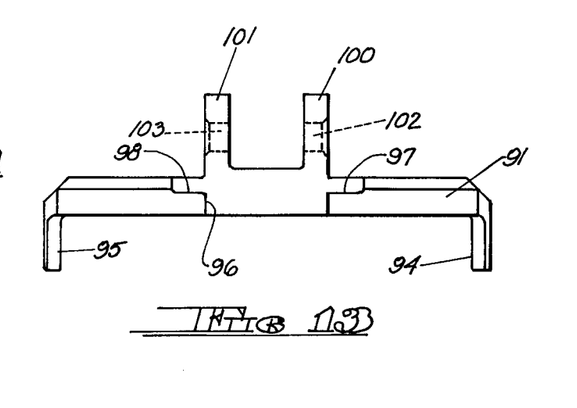
FIG. 13 is an end elevational view, of the retainer plate of FIG. 12.
Figures 14A, 14B, 14D:
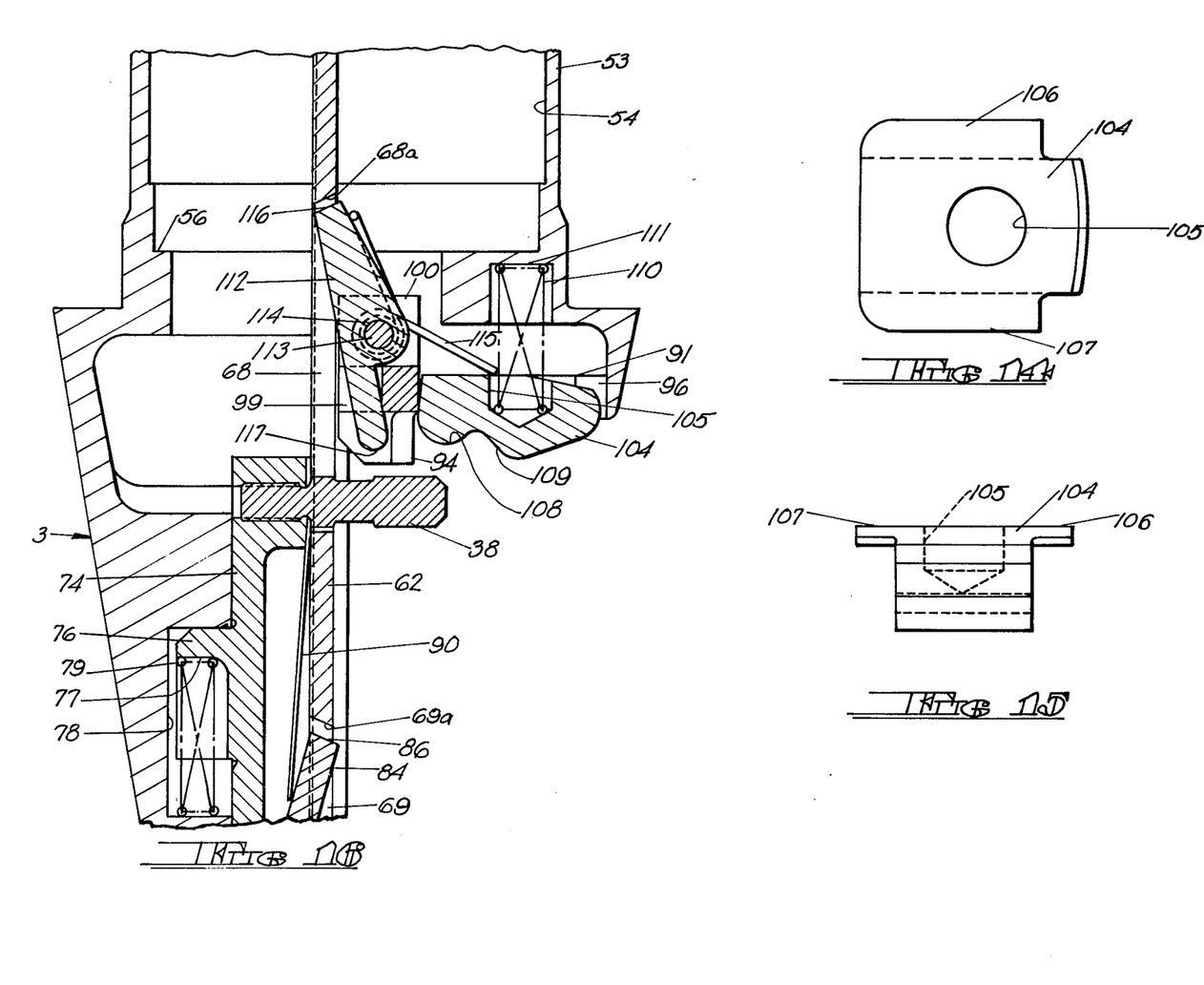
FIG. 14 is a plan view of the staple cartridge latch of the surgical stapling instrument.

Reference is now made to FIGS. 6 and 12 through 16. Below the cylindrical bore 54, a cartridge latch retainer plate 91 is affixed to nose portion 3 of the instrument. The cartridge latch retainer plate 91 is best shown in FIGS. 12 and 13. The retainer plate 91 is a substantially planar member having a pair of perforations 92 and 93 therein for receipt of screws (not shown) by which it is attached to instrument nose portion 3. Near the forward edge of the retainer plate 91, the sides thereof are provided with downwardly depending flanges 94 and 95 which act as guides for the upper end of staple carrying cartridge 18 (FIG. 3). The central portion of the retainer plate 91 has a large notch 96 formed therein flanked by depressed shoulder 97 and 98. The forward edge of the retainer plate 91 has a smaller notch 99 formed therein. The notch 99 is located between a pair of upstanding bifurcations 100 and 101. Bifurcations 100 and 101 have coaxial perforations 102 and 103 formed therein.

The cartridge latch retainer plate 91 is adapted to support a cartridge latch 104. The cartridge latch 104 is most clearly illustrated in FIGS. 14 through 16. The cartridge latch 104 has a central bore 105 extending downwardly from its upper surface. The cartridge latch 104 also has a pair of laterally extending flanges 106 and 107. The bottom of the cartridge latch is configured to provide two pressure points 108 and 109 (FIG. 16) the purpose of which will be described hereinafter.

As will be evident from FIGS. 6 and 12 through 16, the cartridge latch 104 is adapted to be received in the cartridge latch retainer plate notch 96 with the cartridge latch flanges 106 and 107 resting upon the depressed shoulders 97 and 98 respectively. The cartridge latch 104 is urged to its normal position as shown in FIGS. 6 and 16 by a compression spring 110. The lower end of compression spring 110 is received within the bore 105 of the cartridge latch 104, while the upper end of compression spring 10 is received within a socket or bore 111 in the instrument nose portion 3 (see FIGS. 6 and 16).

Pivotally mounted between bifurcations 100 and 101 of the cartridge latch retainer plate 91 there is a lock-out pawl 112. The mounting is accomplished by means of a pivot pin 113 which passes through the perforations 102 and 103 of bifurcations 100 and 101 and through a coaxial perforation 114 in the lock-out pawl 112.

The lock-out pawl 112 is biased to the position illustrated in FIG. 16 by a spring 115 mounted on pivot pin 113. One end of spring 115 rests upon the upper surface of cartridge latch retainer plate 91, while the other end of spring 115 abuts the upper end of the lock-out pawl 112, as can be seen from FIGS. 6 and 16.

The uppermost end of lock out pawl 112 terminates in an abutment surface 116 adapted to cooperate with the slot abutment surface 68a of driver 62, as will be described hereinafter. The lowermost end of lock-out pawl 112 terminates in a nose 117 which extends between the downwardly depending guide flanges 94 and 95 of cartridge latch retainer plate 91. The purpose and operation of lock-out pawl 112 and cartridge latch 104 will be described hereinafter.

Figure 21:
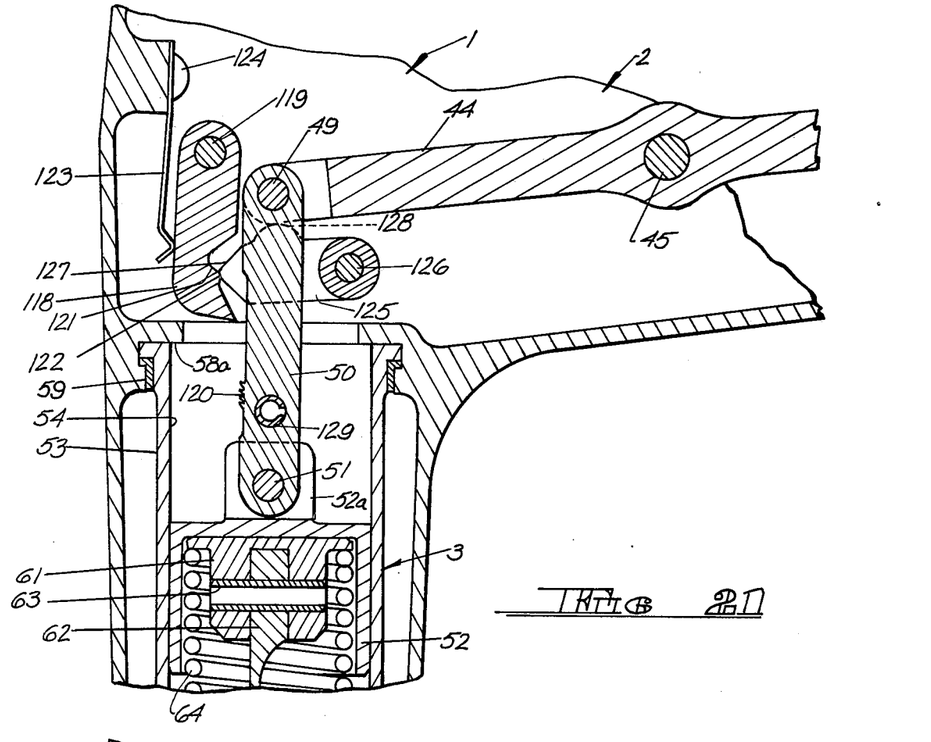
FIG. 21 is an enlarged, fragmentary, cross sectional view showing the components of the drive linkage of the surgical stapling instrument in their respective positions just prior to disengagement of the rachet pawl.

Reference is next made to FIGS. 6 and 21. To complete the structure of the surgical stapling instrument of the present invention a ratchet pawl 118 is pivotally mounted within handle portion 2 by pivot pin 119. Ratchet pawl 118 is adapted to cooperate with ratchet teeth 120 formed on connection rod 50. Ratchet pawl 118 also has cam surfaces 121 and 122 formed therein. The ratchet pawl 118 is biased to its normal position illustrated in FIG. 6 by means of a leaf spring 123. One of leaf spring 123 is affixed to the handle portion 2 of the surgical stapling instrument by a machine screw 124. The free end of leaf spring 123 is adapted to bear upon the ratchet pawl 118 as illustrated. A ratchet latch 125 is pivotally affixed within handle portion 2 by pivot pin 126. The ratchet latch 125 has a nose 127 intended to cooperate with ratchet pawl cam surfaces 121 and 122. The ratchet latch 125 also has a lateral extension 128 intended to cooperate with the main lever 44. Finally, connecting rod 50 is provided with a laterally extending pin 129. Ratchet pawl 118, ratchet teeth 120, ratchet latch 125 and pin 129 all comprise a mechanism assembly to prevent repetition of the staple feed portion of the staple carrying cartridge cycle prior to completion of the staple forming portion of the staple carrying cartridge cycle. The manner in which this is accomplished will be described hereinafter.

The basic elements of the surgical stapling instrument 1 of the present invention having been described, the operation of the instrument may be set forth as follows. The surgical stapling instrument 1 will normally come into the surgical environment without a staple carrying cartridge 18 mounted thereon. Under these circumstances, all of the components of the surgical stapling instrument will be in their at-rest position as illustrated in FIG. 6. In this condition of the instrument, the guide piston 52 is in its fully retracted position within cylindrical bore 54 (with its extension 52a abutting flange 58a) and the driver coupling 61 and driver 62 are in their fully retracted positions as well, all under the influence of compression spring 64. Feeder block 74 and feeder pin 38 are also in their fully retracted positions and feeder pawl 84, under the influence of leaf spring 90 is so positioned that its upper end lies within the elongated slot 69 in driver 62 abutting driver surface 69a. Of particular significance is the position of lock-out pawl 112.

The at-rest condition of lock-out pawl 112 is most clearly shown in the enlarged view of FIG. 16. Under the influence of spring 115, the upper end of lock-out pawl 112 is located within the elongated slot 68 in driver 62. This places the upper abutment surface 116 of lock-out pawl 112 in position to be contacted by the cooperating upper end or abutment surface 68a of elongated slot 68 in driver 62. As a consequence, if a squeezing force is applied to trigger 6 the main lever 44, connecting link 50, guide piston 52 and driver coupling 61 can only advance the driver a short distance until slot surface 68a will contact and abut lockout pawl abutment surface 116. Once contact is established between driver surface 68a and lock-out pawl surface 116, further downward movement of driver 62 is prohibited. This action of the lock-out pawl 112 prevents actuation of the instrument 1 until a staple carrying cartridge 18 is mounted thereon. This action of lock-out pawl 112 further insures that the staple carrying cartridge 18 must be properly mounted on the instrument with driver lug 37 inserted in the driving eyelet 26a of cartridge former 26; feeder pin 38 properly located in driving eyelet 32a of feed actuator 32 of the cartridge and the cartridge properly located on anvil 7.

The first step in the use of the surgical stapling instrument of the present invention is, of course, to mount a staple carrying cartridge 18 thereon. This would normally be done by one of the assisting surgical nurses and is accomplished in the following manner (reference being made to FIGS. 1, 3, 6 and 20). The cartridge 18 is brought toward the instrument nose portion 3 with the staple former housing of the cartridge facing the nose portion 3 of the instrument. The cartridge 18 is brought to the nose portion 3 with the lower end of the cartridge located just above the leg 10 of anvil 7 and with the cartridge 18 angled with respect to the instrument nose portion 3 such that the included angle therebetween is up to about 35°. This is made possible by the undercut 12 on anvil 7. The cartridge 18 is shifted downwardly along nose portion 3 of the instrument until the anvil leg 10 is received within the notch 23 at the bottom of cartridge 18 and the sloping surface 24 of the cartridge contacts the wedge-shaped lug 11 of anvil 7. The cartridge may then be pivoted about the lug 11 of anvil 7 until the exterior surface of the staple former housing 20 of cartridge 18 lies adjacent the instrument nose portion 3. The cartridge 18 is illustrated in its fully mounted position in FIGS. 1 and 20. It may be seen in FIG. 20 that when the cartridge 18 is in its fully seated position, driver lug 37 extends into elongated staple former driving eyelet 26a and feeder pin 38 extends into feed actuator driving eyelet 32a.

Figure 17:
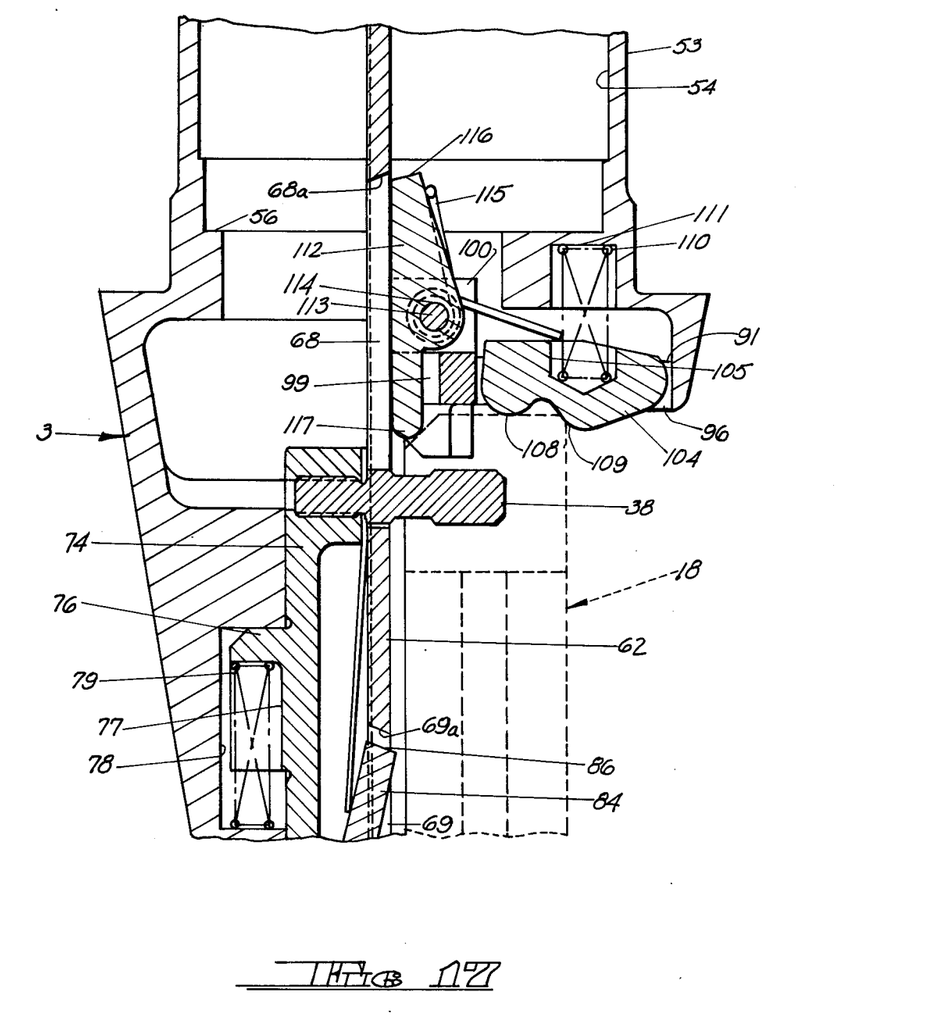
FIG. 17 is an enlarged, fragmentary, cross sectional view showing the staple cartridge latch and the lockout pawl in their respective positions after mounting of a staple cartridge on the instrument nose.

The action of cartridge latch 104 may readily be seen by a comparison of FIGS. 16 and 17. When staple carrying cartridge 18 is rocked into position against instrument nose portion 3, the cartridge latch 104 will shift upwardly against the action of compression spring 110. The cartridge latch 104 will contact the upper end of staple carrying cartridge 18 at the above mentioned pressure points 108 and 109. It will be evident that pressure point 108 will urge the cartridge downwardly against anvil 7. Simultaneously, the pressure point 109, in conjunction with the anvil lug 11 at the other end of the staple carrying cartridge 18, will urge the staple carrying cartridge 18 toward the instrument nose portion 3.

FIGS. 16 and 17 also clearly illustrate the action of lock-out pawl 112. In FIG. 16, in the absence of a staple carrying cartridge 18, the lock-out pawl is in its lock-out position. In FIG. 17, the fully seated staple carrying cartridge 18 contacts nose portion 117 of lock-out pawl 112, maintaining lock-out pawl 112 in its unlocking position against the action of spring 115. The surgical stapling instrument is now ready for use by the surgeon.

For purposes of this explanation, it will be assumed that the tissue in question is skin and that all other surgical procedures have been completed except for the closing of an incision in the skin. Having set the desired rotative position of nose portion 3 with respect to handle portion 2, and using the center line indicators 16 and 17 (FIG. 2) on the front of nose portion 3, the surgeon places the instrument so that the lowermost end of the staple carrying cartridge 18 straddles the incision to be stapled. The surgeon then firmly squeezes trigger 6.

Referring to FIG. 6, as trigger 6 is squeezed, it will rotate about pivot pin 43 in a clockwise direction as viewed in that Figure. This will, in turn, result in a counterclockwise rotation of main lever 44 about pivot pin 45. This action of main lever 44 will cause a downward shifting of connecting rod 50 and guide piston 52. Compression spring 64, acting against driver coupling 61 (which is in abutting relationship with the interior of guide piston 52) is compressed toward spring plate 65. The downward force placed on the guide piston 52 is transferred through driver coupling 61 to the driver 62. As is clearly shown in FIGS. 6 and 17, the at-rest position of feeder pawl 84 is such that, under the influence of leaf sprin 90, it is rotated into the cooperating slot 69 in driver 62. Initial downward movement of driver 62 will cause feeder block 74 and its feeder pin 38 to move downwardly by virtue of the interaction of driver slot abutment surface 69a and feeder pawl abutment surface 86.

As driver 62 continues its downward movement, the rotatable bushing 87 on feeder pawl 84 contacts and rolls along the downwardly and rearwardly sloping interior surface 89 of nose portion 3. Reference is made to FIGS. 6 and 18. It will be noted that as bushing 87 rolls down sloping surface 89, it causes feeder paul 84 to rotate in a counterclockwise direction (as viewed in those Figures) about pivot pin 85 and against the action of leaf spring 90. FIG. 18 illustrates the relationship of these various parts just at the point where feeder pawl 84 is about to be completely rotated out of driver slot 69 and the abutment of feeder pawl surface 86 and driver slot abutment surface 69a is about to be lost. It is at this point that lug 37 of driver 62 just contacts driving eyelet 26a of the cartridge staple former 26.

The downward shifting of feeder block 74 by driver 62 has been accomplished against the action of compression spring 79. At the instant that feeder pawl surface 86 is shifted out of contact with driver slot surface 69a, the feeder block and its feeder pin 38 are free to shift back to their normal, at-rest positions under the influence of compression spring 79. The relationship of the parts at this point is illustrated in FIG. 19.

It will be evident from FIGS. 18 and 19 that the just described downward and return movements of feeder block 74 and feeder pin 38 are very precisely controlled by the interaction of sloping interior nose portion surface 89 and rotatable feeder pawl bushing 87. The initial downward and the return movements of the feeder block 74 and feeder pin 38 result in the actuation of the staple carrying cartridge feeder actuator 32 to accomplish the above described staple feed portion of the cartridge cycle wherein the bottommost staple of the stack is shifted from the cartridge staple feed track 27 to the cartridge staple forming track 25. During this operation, however, since its driving eyelet 26a is elongated, the cartridge staple former 26 has not yet been actuated by the instrument driver lug 37. It will be understood that the transition of the various components from their positions shown in FIG. 18 to their positions shown in FIG. 19 is very rapid.

Continued downward movement of the instrument driver 62 will, by virtue of the engagement between driver lug 37 and staple cartridge former eyelet 26a cause the staple cartridge former 26 to advance the staple in staple forming track 25 to the anvil surface 13 of anvil 7 where it is formed and caused to be implanted in the skin. At the point in time when the surgical staple has just been formed and implanted, the components of the surgical stapling instrument 1, located within nose portion 3 will be in their respective positions illustrated in FIG. 20.

When pressure is removed from the trigger 6, the compression spring 64 will urge the driver coupling 61, the driver 62 and the guide piston 52 upwardly. This action, in turn, will cause the connecting rod 50 to rotate the main lever 44 in a clockwise direction (as viewed in FIG. 6). The main lever 44 will thus return the trigger to its initial at-rest position as shown in FIG. 6.

Just prior to the driver 62 reaching the limit of its upward movement, the feeder pawl 112, under the influence of leaf spring 90, will rotate into its initial position within elongated driver slot 69. When the driver 62 reaches its uppermost position the operational cycle of the surgical stapling instrument 1 is complete and all of the instrument components are in their initial, at-rest positions as illustrated in FIG. 6. The operational cycle of the surgical stapling instrument 1 may now be repeated.

Once feeder block 74 and its feeder pin 38 have completed their cycle resulting in the location of a staple in the staple forming track 25 of staple carrying cartridge 18, it is important that the feeder block and feeder pin cycle not be repeated until the overall cycle of the surgical stapling instrument 1 has been completed to cause the forming and implanting of that staple within the cartridge staple forming track 25. As can best be seen in FIG. 6, at the initiation of the instrument cycle the ratchet pawl 118, under the influence of leaf spring 123, is in position to cooperate with the ratchet teeth 120 on connecting rod 50. During the initial portion of the instrument cycle, while the driver 62 is moving the feeder block 74 and feeder pin 38 downwardly, the ratchet pawl 118 in cooperation with ratchet teeth 120 prevent the driver 62 and associated components from reversing their direction and shifting upwardly, even if the trigger 6 is completely released by the surgeon.

Immediately after the feeder pawl 84 disengages the driver 62, allowing feeder block 74 and feeder pin 38 to return to their original positions (as described above), ratchet pawl 118 will have passed the last of the ratchet teeth 120. If, for any reason, the trigger is released from this point on and prior to completion of the full instrument cycle, the driver 62 would return to its position just after disengagement of feeder pawl 84 (its position shown in FIG. 19), but would not return sufficiently to allow feeder pawl 84 to reenter driver slot 68 and reengage driver slot surface 68a. This feature prevents the feeding of another staple within the staple carrying cartridge 18 before the staple already within the cartridge staple forming track 25 has been formed and implanted. Near the very end of the instrument cycle, the end of main lever 44 (near its attachment to connecting rod 50) comes into contact with the lug 128 on ratchet latch 125. This causes the ratchet latch 125 to rotate counterclockwise about its pivot pin 126 (as viewed in FIG. 6). The tip of ratchet latch 125 shifts along cam surface 121 of ratchet pawl 118 until it reaches cam surface 122 of the ratchet pawl. This shifts the ratchet pawl 118 to a position where it is no longer effective to cooperate with ratchet teeth 120 and maintains the ratchet pawl in that position. FIG. 21 illustrates the ratchet latch nose 127 shifting along cam surface 121 toward cam surface 122 on ratchet pawl 118.

Figure 22:
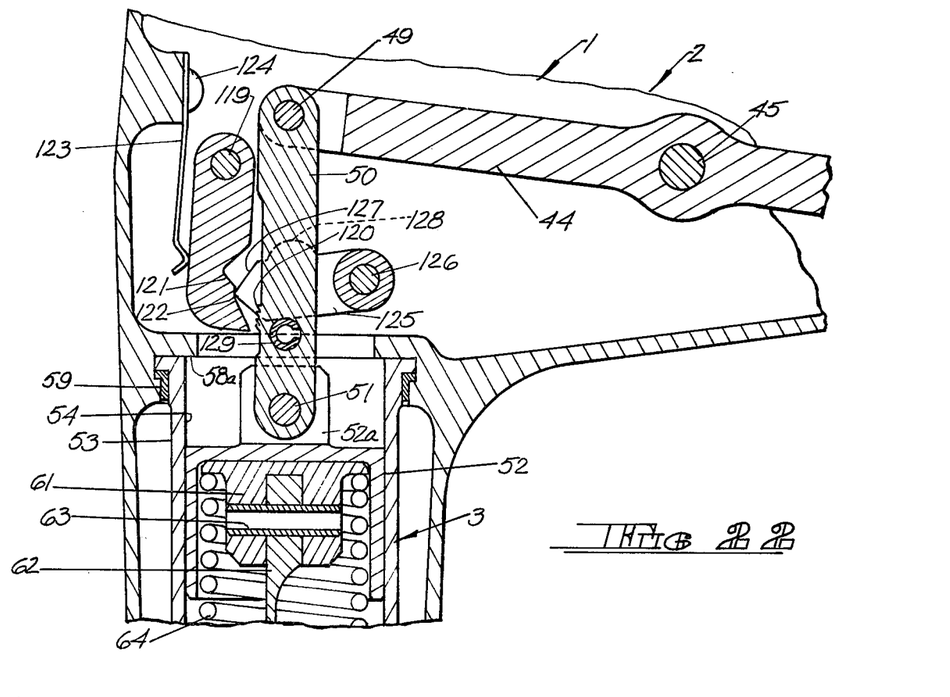
FIG. 22 is an enlarged, fragmentary, cross sectional view showing the components of the drive linkage in their respective positions just prior to reengagement of the ratchet pawl.

As indicated above, when pressure is removed from the instrument trigger 6, the compression spring 64 will urge the driver coupling 61, driver 62 and guide piston 52 upwardly. This action, in turn, will cause the connecting rod to rotate main lever 44 to return to its initial at-rest position shown in FIG. 6. Just prior to the guide piston extension 52a reaching the handle portion flange 58a pin 129 in connecting link 50 will contact ratchet latch 125. This is shown in FIG. 22. This action is simultaneous with the return of the feeder pawl 84 into the elongated slot 69 of driver 62. It will be evident from FIG. 22 that as the extension 52a of guide piston 52 moves further upwardly until it abuts the handle portion shoulder 58a signaling the end of the instrument cycle, pin 129 in connecting rod 50 will shift ratchet latch 125 upwardly about its pivot pin 126. The nose portion 127 of ratchet latch 125 will return to the position illustrated in FIG. 6 allowing ratchet pawl 118 to achieve its initial at-rest position.

Modifications may be made in the invention without departing from the spirit of it.

The embodiments of the invention in which an exclusive property or privilege is claimed are defined as follows:

1. A surgical stapling instrument for use with a surgical staple carrying cartridge of the type having a staple feeding track containing a stack of surgical staples, a parallel staple forming track, a longitudinally shiftable feeder actuator operative to cause the lowermost staple of the stack to be shifted from said staple feeding track to said staple forming track and a longitudinally shiftable staple former to implant and form said staple, said surgical stapling instrument comprising a handle portion and a nose portion, an anvil having an anvil surface about which said surgical staples are formed being mounted at the free end of said nose portion, means to releasably mount said staple carrying cartridge on said nose portion and said anvil, means in said instrument nose portion to longitudinally shift said feeder actuator to feed the lowermost surgical staple of said stack to said staple forming track, said means to shift said cartridge feeder actuator comprising a feeder block mounted in said nose portion so as to be longitudinally shiftable therein between a normal and an extended position and so as to be operatively connectable to said cartridge feeder actuator, means in said instrument nose portion to longitudinally shift said cartridge staple former to form said surgical staple about said anvil surface, said staple former shifting means comprising a driver mounted in said nose portion so as to be longitudinally shiftable therein between a normal and an extended position and so as to be operatively connectable to said cartridge staple former, a trigger mounted in said handle portion and operatively connected to said driver to shift said driver from its normal position to its extended position to cause said staple former to form a surgical staple about said anvil surface when pressure is manually applied to said trigger, means initially connecting said feeder block to said driver to cause said driver to shift said feeder block from its normal position to its extended position during initial movement of said driver toward its extended position to operate said cartridge feeder actuator prior to operation of said staple former by said driver, means to release said feeder block from said driver upon actuation of said cartridge feeder actuator, first biasing means to return said released feeder block to its normal position and second biasing means to return said driver to its normal position upon release of said trigger after formation of a surgical staple.

2. The structure claimed in claim 1 wherein said means to releasably mount said staple carrying cartridge on said instrument nose portion comprises a resilient latch, said latch being configured to releasably engage the upper end of said staple carrying cartridge in such a way as to urge said cartridge into abutment with both said nose portion and said instrument anvil.

3. The structure claimed in claim 1 including means in said nose portion to prevent reactivation of said staple feeder actuator until said shifting of said staple former has been completed.

4. The structure claimed in claim 1 wherein said nose portion is rotatively mounted in said handle portion and may be set at and will remain in any rotative position with respect to said handle portion.

5. The structure claimed in claim 1 including lock-out means to prevent shifting of said instrument driver in the absence of a cartridge on said nose portion.

6. The structure claimed in claim 1 including means to prevent said connecting means from again connecting said feeder block to said driver until said driver has been fully shifted to its extended position.

7. The structure claimed in clam 1 wherein said driver comprises an elongated plate-like member having upper and lower ends, said upper driver end being operatively connected to said trigger, said driver having a laterally extending lug near said lower driver end and engagable in an elongated eyelet in said cartridge staple former, said driver having a first elongated slot therein, said feeder block comprising an elongated block-like element located adjacent said driver and having upper and lower ends, a laterally extended feeder pin being mounted on said feeder block near said upper end thereof, said feeder pin extending through said first slot in said driver and being engagable with an eyelet in said cartridge feeder actuator, said driver having a second elongated slot between said first slot and said driver lug, said means to initially connect said driver and said feeder block comprising a feeder pawl having upper and lower ends, said feeder pawl being pivotally connected intermediate its upper and lower ends to said lower end of said feeder block, said feeder pawl having a roller pivotally mounted on its lower end, said feeder pawl being pivotable between a first position wherein said upper end of said feeder pawl extends into and engages said second driver slot connecting said feeder block and said driver and a second position wherein said upper end of said feeder pawl lies outside said second driver slot, spring means biasing said feeder pawl to said first position, said means to release said feeder block from said driver comprising a cam surface in said nose portion engagable by said roller and so configured as to shift said feeder pawl via said roller from its first position to its second position releasing said feeder block from said driver at the time said driver lug engages the lower end of said elongated cartridge staple former eyelet to shift said staple former toward said anvil.

8. The structure claimed in claim 7 including lock-out means to prevent shifting of said instrument driver in the absence of a cartridge on said nose portion, said lock-out means comprising a lock-out pawl having upper and lower ends and being pivotally mounted within said nose portion intermediate its upper and lower ends, said pawl being shiftable between a lock-out position and an unlocking position, when said lock-out pawl is in said lock-out position its upper end extends into said first elongated slot in said driver precluding shifting of said driver and and its lower end extends outwardly of said nose portion into a position normally occupied by a portion of said staple carrying cartridge, when said lock-out pawl is in said unlocking position its upper end lies outside said first driver slot and its lower end is within the confines of said nose portion permitting shifting of said driver, means to bias said lock-out pawl to said lock-out position, said lock-out pawl being shiftable to said unlocking position by a staple carrying cartridge, said lower end of said lock-out pawl abutting the staple carrying cartridge to maintain said lock-out pawl in said unlocking position when said staple carrying cartridge is properly mounted on said instrument nose portion and said anvil.

9. The structure claimed in claim 7 wherein said instrument nose portion has an upper hollow cylindrical end captively mounted in said handle portion, said cylindrical nose end having an upper edge in abutment with an annular flange in said handle portion, the lowermost portion of said cylindrical nose end having an internal annular shoulder, a guide piston slidably mounted in said cylindrical nose end, said upper end of said driver extending into said cylindrical nose end and having a coupling member affixed thereto, an annular spring plate mounted on said internal annular shoulder of said cylindrical nose end, a compression spring located within cylindrical nose end and about said driver, said compression spring abutting said spring plate and said driver coupling, said driver coupling member being constantly in abutting relationship with said guide piston by virtue of said compression spring, said guide piston normally being in abutting relationship with said annular flange in said handle portion by virtue of said compression spring and thus determining said normal position of said driver, said trigger being operatively connected to said guide piston such that when pressure is applied to said trigger it will shift said guide piston away from said annular flange and against the action of said compression spring to shift said driver from its normal position to its extended position, said compression spring comprising said second biasing means to return said driver to its normal position upon release of said trigger after formation of a surgical staple.

10. The structure claimed in claim 8 including a lever and a connecting link operatively connecting said trigger to said guide piston, said trigger being pivotally mounted within said handle portion, said lever being pivotally mounted intermediate its ends within said handle portion, said connecting link being located within said handle portion, one end of said connecting link being pivotally attached to said guide piston, the other end of said connecting link being joined by a pivot pin to one end of said lever, the other end of said lever being pivotally connected to said trigger, whereby when pressure is applied to said trigger it will rotate about about its pivotal mounting resulting in rotation of said lever about its pivotal mounting, such rotation of said lever shifting said connecting link and said guide piston against the action of said compression spring thereby shifting said driver from its normal to its extended position.

11. The structure claimed in claim 10 including ratchet teeth on said connecting link, a ratchet pawl pivotally mounted within said handle portion and swingable between a first ratchet tooth engaging position and a second ratchet tooth non-engaging position, spring means biasing said ratchet pawl to its first position, a ratchet pawl latch pivotally mounted within said handle portion, said ratchet pawl latch being so positioned that when said driver reaches its extended position it will be contacted and pivoted by said lever from a first normal position to a second position wherein it contacts and shifts said ratchet pawl to its second position, a laterally extending pin mounted on said connecting link, said pin being so located on said connecting link as to contact and shift said ratchet pawl latch from it second position to its first position upon return of said driver to its normal position, whereby said ratchet pawl and said ratchet pawl latch cooperate to prevent shifting of said driver to its normal position from any position other than its extended position so that said cartridge feeder actuator cannot be operated until the surgical staple last fed thereby from said staple feeding track to said staple forming track has been formed by said cartridge staple former.

12. The structure claimed in claim 1 wherein said instrument nose portion has an upper hollow cylindrical end captively mounted in said handle portion, said cylindrical nose end having an upper edge in abutment with an annular flange in said handle portion, the lowermost portion of said cylindrical nose end having an internal annular shoulder, a guide piston slidably mounted in said cylindrical nose end, said upper end of said driver extending into said cylindrical nose end and having a coupling member affixed thereto, an annular spring plate mounted on said internal annular shoulder of said cylindrical nose end, a compression spring located within said cylindrical nose end and about said driver, said compression spring abutting said spring plate and said driver coupling, said driver coupling member being constantly in abutting relationship with said guide piston by virtue of said compression spring, said guide piston normally being in abutting relationship with said annular flange in said handle portion by virtue of said compression spring and thus determining said normal position of said driver, said trigger being operatively connected to said guide piston such that when pressure is applied to said trigger it will shift said guide piston away from said annular flange and against the action of said compression spring to shift said driver from its normal position to its extended position, said compression spring comprising said second biasing means to return said driver to its normal position upon release of said trigger after formation of a surgical staple.

13. The structure claimed in claim 12 wherein said upper hollow cylindrical end of said nose portion is rotatively mounted in said handle portion in such a way that said nose portion can be oriented in any rotative position about its longitudinal axis throughout 360° with respect to said handle portion.

* * * * *